United States Patent [19]

Hohorst et al.

[11] Patent Number: 4,770,870
[45] Date of Patent: Sep. 13, 1988

[54] METHOD FOR REDUCING PAIN ASSOCIATED WITH THE ADMINISTRATION OF 4-SULFIDO-OXAZAPHOSPHORINES AND 4-SULFOALKYLTHIO-OXAZAPHORPHORINES

[75] Inventors: Hans-Jurgen Hohorst, Marburg-Marbach; Gernot Peter, Nidderau; Georg Voelcker, Nidderau-Windecken; Erhardt Wrabetz, Frankfurt am Main, all of Fed. Rep. of Germany

[73] Assignee: Asta Pharma Aktiengesellschaft, Frankfurt am Main, Fed. Rep. of Germany

[21] Appl. No.: 714,845

[22] Filed: Mar. 22, 1985

Related U.S. Application Data

[63] Continuation-in-part of Ser. No. 454,865, Dec. 30, 1982.

[30] Foreign Application Priority Data

Dec. 31, 1981 [DE] Fed. Rep. of Germany ....... 3151977
Nov. 6, 1982 [DE] Fed. Rep. of Germany ....... 3222006

[51] Int. Cl.⁴ .............................................. A61K 31/66
[52] U.S. Cl. ...................................... 424/10; 514/105
[58] Field of Search ........................... 424/10; 514/105

Primary Examiner—Jerome D. Goldberg
Attorney, Agent, or Firm—Cushman, Darby & Cushman

[57] ABSTRACT

Through the combined use of a 4-sulfido-oxazaphosphorine of the formula:

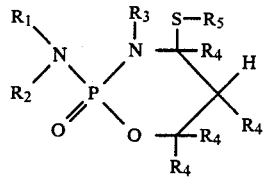

wherein $R_1$, $R_2$, and $R_3$ are hydrogen, methyl, ethyl, 2-chloroethyl or 2-methanesulfonyloxyethyl and at least two of them are taken from the group consisting of 2-chloroethyl and 2-methanesulfonyloxyethyl, $R_4$ is hydrogen or methyl, $R_5$ is a $C_2$–$C_6$-hydroxyalkyl group or a $C_2$–$C_6$-mercaptoalkyl group of each of these groups with an additional mercapto group, or $R_5$ is a carboxy-$C_1$–$C_{10}$ alkyl group, a carb-$C_1$–$C_6$-alkoxy-$C_1$–$C_{10}$-alkyl group, a 2-amino-2-carboxyethyl group, a 2-amine-2-carb-$C_1$–$C_6$-alkoxy-ethyl group, a 2-$C_2$–$C_6$-alkanoylamino-2-carboxyethyl group, the glutathionyl group, a $C_2$–$C_6$-sulfoalkyl group or a $C_2$–$C_6$-sulfoalkyl group which contains a mercapto group or a physiologically compatible salt thereof in combination with a thion compound of the formula:

$$R_6SR_7 \qquad II$$

where $R_6$ is the glutathionyl group or a $C_2$–$C_6$-alkyl group which is substituted once or twice by a hydroxy group, mercapto group, amino group, a $C_2$–$C_6$-alkanoylamino group, sulfo group, a carbo-$C_1$–$C_6$-alkoxy group or carboxy group and $R_7$ is hydrogen or $R_7$ is a $C_2$–$C_6$-sulfoalkylthio group if $R_6$ represents a $C_2$–$C_6$-sulfoalkylthio group or a physiologically compatible salt of the compound of formula II, there is an improvement over known compounds in the chemotherapy of cancer illnesses, especially in having reduced toxicity and side effects. When a compound of formula II is administered simultaneously with a compound of formula I by way of a vein the normal pain associated with the administering of the compound of formula I is prevented.

23 Claims, No Drawings

METHOD FOR REDUCING PAIN ASSOCIATED WITH THE ADMINISTRATION OF 4-SULFIDO-OXAZAPHOSPHORINES AND 4-SULFOALKYLTHIO-OXAZAPHORPHORINES

CROSS REFERENCE TO RELATED APPLICATION

This application is a continuation-in-part application of Ser. No. 454,865, filed Dec. 30, 1982.

BACKGROUND OF THE INVENTION

Compounds of the general formula:

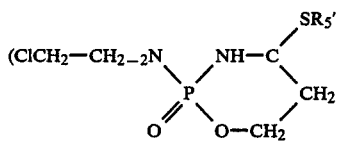

where $R_5'$ is the group $-(CH_2)_n-OH$ and n is 2, 3, 4, or 6 are known. These compounds have an antitumor activity but at the same time are very toxic (see Hirano, Tetrahedron Letters No. 10 (1979) pages 883–886; Peter, Cancer Chemother. Pharmacol. 3 (1979) pages 181–188).

Furthermore, in Draeger, Cancer Treatment Reports 60 (1976) pages 355–359, there is described the formation of compounds of the formula:

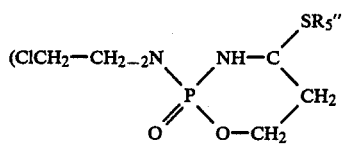

where $R_5''$ is the group $-CH_2-CH-(NH_2)-COOH$ or $-CH_2CH(NHCOCH_3)-COOH$ from 4-hydroxy-cycliphosphamide and cysteine, N-acetyl cysteine or glutathione.

The entire disclosures of the Hirano, Peter, and Draeger articles are hereby incorporated by reference and relied upon.

SUMMARY OF THE INVENTION

The invention is directed to compositions for combatting cancer and for immune suppression comprising a 4-sulfido-oxazaphosphorine of the general formula:

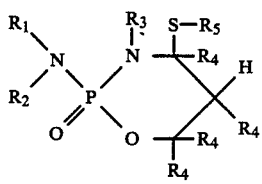

where $R_1$, $R_2$, and $R_3$ are the same or different and are hydrogen, methyl ethyl, 2-chloroethyl,1 or 2-methanesulfonyloxyethyl and at least two of them are 2-chloroethyl and/or 2-methanesulfonyloxyethyl, $R_4$ is hydrogen or methyl, $R_5$ is a $C_2-C_6$-hydroxyalkyl group or a $C_2-C_6$-mercaptoalkyl group or each of these groups also has an additional mercapto group, or $R_5$ is a carboxyl-$C_1-C_{10}$ alkyl group, a carb-$C_1-C_6$-alkoxy-$C_1-C_{10}$-alkyl group, a 2-amino-2-carboxyethyl group, a 2-amino-2-carb-$C_1-C_6$-alkoxy-ethyl group, a 2-$C_2-C_6$-alkanoylamino-2-carboxyethyl group, a 2-$C_2-C_6$-alkanoylamino-2-carb-$C_1-C_6$-alkoxy-ethyl group, the glutathionyl group, a $C_2-C_6$sulfoalkyl group or a $C_2-C_6$-sulfoalkyl group which contains a mercapto group or a physiologically (or pharmaceutically) compatible salt thereof in combination with a thio compound of the formula $$R_6SR_7 \qquad II$$

where $R_6$ is the glutathionyl group or a straight or branch chain $C_2-C_6$-alkyl group which is substituted once or twice by a hydroxy group, mercapto group, amino group, a $C_2-C_6$-alkanoylamino group, sulfo group, carb-$C_1-C_6$-alkoxy group, or carboxy group and $R_7$ is hydrogen or $R_7$ is a $C_2-C_6$-sulfoalkylthio group if $R_6$ represents a $C_2-C_6$-sulfoalkylthio group or a physiologically (or pharmaceutically) compatible salt of the compound of formula II. Preferably $R_6$ is an unsubstituted $C_2-C_6$-sulfoalkyl group or the compound of formula II is cysteine, N-acetylcysteine, cysteine hydrochloride, cysteine ascorbate, N-acetyl homocysteine, penicillamine or 2,3-dimercapto-1-propanol.

The compositions of the invention are useful as medicines. The medicines can contain, for example, between 0.5 and 3500 mg of the 4-sulfido-oxaphosphorine of formula I and 0.2 to 10 moles (in mg) of the thio compound of formula II based on 1 mole of the 4-sulfido-oxaphosphorine. The compositions can contain the customary pharmaceutical carriers and/or diluents.

The compositions of the invention can be packaged as two separate galenic preparations:

(a) contains at least one 4-sulfido-oxaphosphorine of formula I or a physiologically compatible salt thereof alone or together with a customary pharmaceutically acceptable carrier and/or diluent, and (b) contains at least one thio compound of formula II or a physiologically compatible salt thereof alone or together with a customary pharmaceutical carrier and/or diluent.

The compositions or therapeutic package can be prepared by mixing the 4-sulfido-oxaphosphorine of formula I or its physiologically compatible salt and the thio compound of formula II or its physiologically compatible salt, alone or together, with customary pharmaceutical carriers or diluents.

The compounds of formula I are cytostatic and for example when $R_1$ and $R_2$ in each case, are 2-chloroethyl and $R_3$ and $R_4$ are hydrogen and $R_5$ is a 2-sulfoalkyl group $(-CH_2-CH_2-SO_3H)$, for example as a cyclohexylamine salt or a lysine salt when injected in a vein gives a severe long-lasting pain. Apparently this pain is due to a specific reaction of the compound of formula I with sensitive nerve-ending or pain receptors. The pain is not the result of a inflammatory tissue reaction. It occurs even with no histologically detectable tissue damage. Surprisingly this pain is prevented by the use, e.g. simultaneously of the compound of formula II, for example 2-mercapto-ethanesulfonic acid in the form of sodium salt or N-acetyl cysteine. There can also be employed the other compounds of formula II and especially the preferred compounds mentioned above.

The amount of compound of formula II should be sufficient to reduce the pain associated with injecting the compound of formula I into the vein.

In order to reduce the venus pain the compound of formula I can be admixed with the thio compound of formula II shortly prior to administration, or the compound of formula I and the thio compound of formula I can be through a common line from separate containers and then administered through the opening of an injection needle. They can be administered to humans and other animals, e.g., dogs, cats, horses, cattle, sheep. For such use the amount of the thio compound of formula II can be 1–10 molar times, preferably 2 to 6 molar times, especially 3–5 molar times, e.g. 4 molar times the amount of compound I.

The compounds of formula I where not over one of $R_1$ and $R_2$ is 2-chloroethyl are novel. When used by themselves, with or without a pharmaceutical carrier and/or diluent they can be used as a medicine in an amount between 0.2 and 1500 mg.

The compounds of formula I can be prepared for example by reacting a 4-hydroxy or 4-$C_1$-$C_4$- alkoxy-oxazaphorine of the general formula

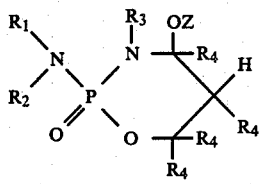   III where $R_1$, $R_2$, $R_3$, and $R_4$ are as defined above and Z is hydrogen or $C_1$-$C_4$ alkyl with a compound of the general formula:

$$HSR_5 \qquad\qquad IV$$

where $R_5$ is as defined above and in a given case, the compound formed is converted into a salt. Compounds of formula I where $R_1$ and $R_2$ both are chloroethyl, $R_3$ and $R_4$ are both hydrogen and $R_5$ is a straight unsubstituted $C_2$-$C_4$-hydroxyalkyl group, a straight unsubstituted $C_6$-hydroxyalkyl group, a carboxy-$C_1$-$C_{10}$-alykl group, the glutathionyl group, the group —CH$_2$—CH(NH$_2$)—COOH or the group —CH$_2$—CH(NH—CO—CH$_3$)—COOH are prepared by reacting a 4-$C_1$-$C_4$- alkoxy-oxaphosphorine of the general formula:

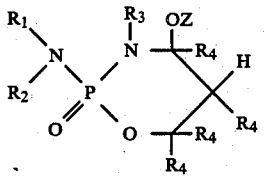   III where Z is a $C_1$-$C_4$-alkyl group with a compound of the formula IV where $R_5$ is a straight $C_2$-$C_4$-hydroxyalkyl group, a straight —CH$_6$-hydroxyalkyl group, the glutathionyl group, the group —CH$_2$—CH(NH$_2$)—COOH or the group —CH$_2$—CH(NH—CO—CH$_3$)—COOH and in a given case, converting the compound into a salt.

Through the use of the compound of formula I with the compounds of formula II or the other mentioned thio compounds, there is obtained a good cancerotoxic activity (i.e. effectiveness against cancer) while simultaneously a considerable reduction in the general toxicity (e.g. compared to the use of the compound of formula I alone), so that through the combination of the invention there becomes possible a favorable local regional chemotherapy and an optimized systemic chemotherapy of cancer.

The compounds of formula I can be present in various steroisomeric forms, for example, as racemate, as optically active compounds or as diastereomers (cis and trans forms). Under the compounds of formula I there is understood to be included all of the possible stereoisomers. The production of such compounds of formula I can take place for example, according to the methods given in German patent application No. P 3220432.9 and German Pat. No. P 3111428.8 and related Scheffler U.S. application Ser. No. 356,636, filed Mar. 10, 1982. The entire disclosures of both German applications and the Scheffler U.S application are hereby incorporated by reference and relied upon. There can be employed in the present invention any of the oxazaphosphorin-4-thio-alkanesulfonic acids or salts mentioned in Scheffler.

The hydroxyalkyl group, the mercaptoethyl group, the carboxy-$C_1$-$C_{10}$ alkyl groups as well as the sulfoalkyl group (the group -alkyl-$SO_3H$) in the compound of formula I and formula II can be straight or branched. Illustrative of such groups are hydroxyethyl, 3-hydroxypropyl, 2-hydroxypropyl, 4-hydroxybutyl, 3-hydroxybutyl, 2-methyl-3-hydroxypropyl, 5-hydroxyamyl, 6-hydroxyhexyl, 2-mercaptoethyl, 3-mercaptopropyl, 2-mercaptopropyl, 4-mercaptobutyl, 5-mercaptoamyl, 6-mercaptohexyl, carboxymethyl, carboxyethyl, 3-carboxypropyl, 4-carboxybutyl, 2-methyl-3-carboxypropyl, 5-carboxyamyl, 6-carboxyhexyl, 7-carboxyheptyl, 8carboxyoctyl, 9-carboxynonyl, 10carboxydecyl, 2-methyl-8-carboxyoctyl, sulfoethyl, 3-sulfopropyl 4-sulfobutyl, 5-sulfoamyl and 6-sulfohexyl. The hydroxy group, the mercapto group, the carboxy group as well as the sulfonic acid group is preferably located in the ω-position of each alkyl group. It is especially a matter of an alkyl group having 2–4, preferably 2, carbon atoms. Likewise, the $C_2$-$C_6$-alkyl group of the compounds of formula II preferably has 2–4 carbon atoms. Examples of such $C_2$-$C_6$-alkyl groups are ethyl, propyl, isopropyl, butyl, sec.butyl, t-butyl, amyl and hexyl. By the term glutathionyl group there is understood the univalent group obtained from glutathione by the removal of the SH group.

In case $R_5$ is a 2-$C_2$-$C_6$-alkanoyl-amino-2-carboxyethyl group the alkanoyl can be for example, acetyl, propionyl, butyryl, isobutyryl, tert.butyryl, valeryl, or caproyl. What is true in regard to the $C_2$-$C_6$-alkanoyl group is true if the group $R_6$ of formula II is a $C_2$-$C_6$-alkyl group which is substituted by a $C_2$-$C_6$-alkanoylamino group.

In case in formula II the group $R_7$ is a $C_2C_6$-sulfoalkylthio group, it is a matter of the dithio-di-$C_2$-$C_6$-alkanesulfonic acids of formula HO—$SO_2$—alkyl—S—S—alkyl—$SO_2$—OH, whereby alk is a straight chain or branched alkylene group having 2-6 carbon atoms, e.g. ethylene, propylene, trimethylene, tetramethylene, pentamethylene or hexamethylene, perferably alk is the group —CH$_2$—CH$_2$.

The mercapto group located on the $C_2$-$C_6$-sulfoalkyl group (group $R_5$ of formula I) for example, is on the 1-, 2-, 3-, 4-, or 5- carbon atom of the alkylene chain (counting beginning from the sulfonic acid group). The mercapto group, however, cannot be located on the carbon atom of the alkylene chain which produces the bond with the oxazaphosphorinyl-4-thio-group.

It is especially a matter of those compounds of formula I wherein $R_5$ is as defined and the groups $R_1-R_4$ have the following meanings:

$R_1$ and $R_2$=2-chloro-ethyl, $R_3$ and $R_4$=H;
$R_1$, $R_2$, and $R_3$=2-chloro-ethyl, $R_4$=H;
$R_1$ and $R_3$=2-chloro-ethyl, $R_2$ and $R_4$=H;
$R_1$=2-methylsulfonyloxy-ethyl, $R_3$=2-chloro-ethyl, $R_2$ and $R_4$=H.

As thio compounds of formula II there especially come into question compounds of formula II where $R_7$ is hydrogen.

In case the compounds of formula I contain a sulfonic acid group there can also be used therapeutically usable salts of the compounds of formula I which are formed through salt formation with this sulfonic acid group. There are especially considered in these cases the alkali (e.g. potassium sodium), alkaline earth (e.g. calcium, magnesium), or ammonium salts. In the case of the ammonium salts there are also especially included the ammonium salts of which 1, 2, or 3 H-atoms can be substituted by methyl, ethyl, or 2-hydroxyethyl groups or derived from the following amines: guanidine, morpholine, cyclohexylamine, ethylenediamine, piperazine. In the case of a dibasic cation or an amine having two monobasic cations (for example ethylenediamine) it is a matter of salts which contains 2 molecules of the sulfonic acid compound corresponding to formula I. The sulfonic acid salts are obtained for example, from the corresponding sulfonic acids of formula I and the corresponding alkali metal or alkaline earth metal hydroxide of ammonia or the corresponding amine in the customary manner for this.

In the case the group $R_6$ of the thio compounds of formula II is a double substituted $C_2-C_6$-alkyl group, this can contain two identical or two different substituents. For example, the following thio compounds come into consideration: 2,3-dimercapto-1-propanol, penicillamine, cysteine, homocysteine, 3-mercapto-1,2-propanediol, 2,3-dimercaptopropanesulfonic acid, 1,2,3-trimercaptopropane, 2-mercapto-ethanesulfonic acid (especially as the sodium salt), 2,2'-dithiodiethanesulfonic acid (especially as the sodium salt).

As salts of the thio compounds there especially come into question those formed from the thio compounds of formula II having acid groups (carboxy groups, sulfoalkyl groups). Hereby it is especially a matter of the corresponding alkali metal salts (Na,K) or ammonium salts. The ammonium salts are derived for example, from ammonia or from the following amines: $C_1-C_4$-mono-, di- or trialkylamines (e.g. trimethylamine, triethylamine, tripropylamine, ethylamine, diethylamine, isopropylamine) which in a given case, can also contain a hydroxy group (for example, mono-, di-, or triethanolamine), ethylene-diamine, choline or betaine. In case the dithio-di-$C_2-C_6$-alkanesulfonic acids are employed as salts there are particularly considered the neutral alkali metal or ammonium salts.

The production of the compounds of formula I can for example take place by reaction of a known 4-hydrogen or 4-alkoxy oxazaphosphorine of formula:

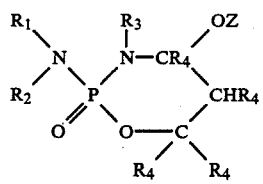

where the groups $R_1$, $R_2$, $R_3$, and $R_4$ are as defined above and Z is hydrogen or a $C_1-C_4$-alkyl group with the corresponding thiol of the formula $HSR_5$ where $R_5$ is as defined above in a solvent, suitably in the presence of an acid catalyst. As acid catalysts there can be used for example: trichloroacetic acid, trifluoroacetic acid, or in general, inorganic or organic acids or also Lewis acids such as $AlCl_3$, $ZnCl_2$, $TiCl_4$ (see Tetrahedron Letters No. 10 (1979), pages 883–886 or also Cancer Chemother. Pharmacol. 3 (1979), pages 181–188).

As solvents for example, there can be used: water, methylene chlorine, alcohols, especially lower alkanols such as methanol, ethanol, propanol, or isobutanol, lower alkyl ketones such as especially acetone, dimethylformamide (DMF) or similar solvents or mixtures of several such solvents. The reaction is carried out for example at a temperature in the range of $-30°$ C. and $+40°$ C., that is optionally with cooling at room temperature or with heating.

In case the group $R_5$ of the compounds of formula I is a $C_2-C_6$-sulfoalkyl group, the corresponding sulfonic acid salts can be obtained through neutralization of sulfonic acid groups with the corresponding base. Furthermore, in such a salt the cation can be exchanged on anion exchanger in known manner for another cation. Naturally the compound III can also be reacted in the manner given above directly with the corresponding sulfonic acid salt of a $C_2-C_6$-sulfoalkyl mercaptan or the salt of a $C_2-C_6$-sulfoalkylmercaptan which contains a further mercapto group. The compounds of formula III which are used as starting materials are known, can be employed as crystalline or as raw products and can be synthesized as follows in known manner:

4-hydroxy-oxazaphosphorines are obtained by reaction of the 4-hydroperoxy derivative (for example A. Takamizawa et al, J. Amer. Chem. Soc., Vol. 95, page 589 (1973), the entire disclosure of which is hereby incorporated by reference and relied upon). 4-alkoxyoxazaphosphorines are formed under acid catasis from the hydroxy derivatives in the corresponding alcohol. The sulfoalkyl thiols can be obtained for example, through reaction of the corresponding sodium bromoalkanesulfonate with thiourea to form thiuronium salt which is split with ammonia. The thus obtained mercaptoalkanesulfonic acid can then be converted into the desired sulfonic acid salt. The racemic cis- and trans-isomers can be produced from the oxazaphosphorine derivatives.

The 4-sulfido-oxazaphosphorines of formula I together with the thio compounds of formula II can be used, for example, in the form of a mixture, a solution or also separated in a capsule, that is together perorally or parenterally. However, the compounds of formulae I and II can also be used separately, that is each itself in the form of a suitable pharmaceutical preparation. In the later case, there is possible a simultaneous administration or an administration at different times. If the compounds of formulae I and II are present in different galenical preparations, both preparations are applied either perorally or parenterally (for example, intravenously or intraperitoneally) for a simultaneous application. In non-simultaneous application, it is recommended to first apply the thio compound of formula II first perorally or parenterally and later to apply the compound I parenterally. Thereby the dispensation of the thio compound II takes place suitably within a time span of about 120 minutes after the dispensation of compound I, preferably 60 minutes before to 30 minutes after, especially 30 minutes before to 10 minutes after dispensation of the compound I, namely, in an amount of at least 1 mole per mole of the amount of the 4-sulfido-oxazaphosphorine I dispensed or to be dispensed up to of the highly compatible dosage of the thio compound II in general up to 10 moles per 1 mole of 4-sulfido-oxazaphosphorine I.

In case the thio compound II is not applied simultaneously with the 4-sulfido-oxazaphosphorine of the formula I, for example the following amounts of thio compound can be administered parenterally or orally:

5 grams: Cysteine (42 millimoles as thio II 60 minutes before application of for example, 1.4 grams of 4-(2-hydroxyethylmercapto)-cyclophosphamide (P1) or 2.3 grams of 3-[2-(bis-(2-chloroethyl)-amine-2-oxo-tetrahydro-2H-1,3,2-oxazaphosphorine-4-yl-thio]-2-mercaptopropanesulfonic acid-cyclohexylamine salt (in the following this compound as "cyclohexylamine salt" is designated as Compound I. The amount of cyclohexylamine salt corresponds in each case to 4.2 millimoles of these two compounds 2.5 grams: Cysteine (21 millimoles) simultaneously with application of 1.4 grams of the compound $P_1$ of 2.3 grams of cyclohexylamine salt.

5 grams: Cysteine 30 minutes after application of 1.4 grams of the compound $P_1$ or 2.3 grams of cyclohexylamine salt.

In the previously mentioned application of the compound before and after application of the 4-sulfido-oxazaphosphorine compound the mole ratio of thio compound II to 4-sulfido-oxazaphosphorine for example is 10:1, with the simultaneous application 5:1. If in place of cysteine there is used another thio compound II, there is calculated the corresponding amount for example, based on the previously given mole ratio. Likewise in place of $P_1$ there can also be used for example, 4.2 millimoles of another 4-sulfido-oxazaphosphorine of the formula I or a corresponding salt thereof.

In intravenous application of the 4-sulfido-oxazaphosphorine I the duration of injection should be longer than 1 minute, for example, 2 to 10 minutes. The applied volume of injection should in parenteral application (for example, intravenous or intraperitoneal) be per injection about 0.5 to 100 ml, that is there are used the lowest possible concentrated solutions of the 4-sulfido-oxazaphosphorine, for example 0.1 to 7% solutions, preferably 0.5 to 2% solutions, of the 4-sulfido-oxazaphosphorine I. Preferably the thio compounds of formula II as well as the 4-sulfido-oxazaphosphorine are dispensed parenterally. This is true both the separate and for the common application of the two compounds.

The combination of the compounds of formula I with the thio compounds of the invention for example, at intraperitoneal injection with the NMRI-mouse (mouse strain which was bred by the National Medical Research Institute and is obtainable in the commerce of research animals) at the third day after transplantation of S180 cancer cells ($10^6$ tumor cells/mouse) exhibits a good cytostatic effect (method according to Goldin, Johnson, Venditti, Preclinical, Characterization of Candidate Antitumor Drugs, Cancer Chemotherapy Report, Part 2, Vol. 5, 1975).

For example, with the above-mentioned test methods at a single dosage of 32 mg/kg of 4-(2-hydroxy-ethylmercapto)-cyclophosphamide (=$P_1$) and 58 mg/kg of cysteine there is obtained a healing of 50% of the tumor bearing animals, at a dosage of 220 mg/kg $P_1$ and 392 mg/kg cysteine 95% of the animals were healed. A single dosage of 52 mg/kg of cyclohexylamine salt and 47 mg/kg of cysteine with the same test methods likewise effects a healing of the majority of the tumor bearing animals.

The cytostatic action is comparable with that of the known medicine cyclophosphamide.

The lowest cancerotoxic effective dosage in the above stated animal experiments for example in the case of 4-(2-hydroxy-ethylmercapto)-cyclophosphamide ($P_1$) and cysteine is 5 mg/kg $P_1$ and 9 mg/kg cysteine intraperitoneally, in the case of the combination cyclohexylamine salt/cysteine is 8.2 mg/kg cyclohexylamine salt and 7.4 mg/kg cysteine intraperitoneally.

As a general dosage range for the action in the above animal experiments there comes into question for example, a dosage between 10 mg/kg of compound I and 9–18 mg/kg thio compound II to 400 mg/kg compound I and 360–720 mg/kg compound II, especially dosages between 50 mg/kg compound I and 45–85 mg/kg thio compound II and 400 mg/kg compound I and 360–720 mg/kg thio compound II.

Finally, through the combination of the invention there is producible a practically complete disappearance of the known urotoxic side effect of the oxazaphosphorine which is the limiting factor of the chemotherapy with oxazaphosphorines even before the bone marrow toxicity.

Thus, for example, the $LD_{50}$ (the $LD_{50}$ is that dosage which lead to the death of 50% of the animals employed) of 4-(2-hydroxy-ethylmercapto)-cyclophosphamide increases with slower intravenous or intraperitoneal dosage in the mouse to 3–4 fold (in the case of application of the cyclohexylamine salt to 2–3 fold) if the injection takes place in the presence of a 5 fold molar excess of cysteine. Thereby the cytotoxic effective against L 1210 cancer cells (lymphatic leukemia cells of the mouse which are used as standard cancer cells for test purposes and are obtainable in tumor banks (for example, Deutsch Krebsforschungszentrum in Heidelberg, Germany) or commercially) in vitro or L 1210 and S180 cancer cells in vivo in intraperitoneal use is only slightly reduced. Therewith there results through the combination of the invention a doubling to triple the therapeutic breadth in comparison to the single use of the 4-(2-hydroxy-ethylmercapto)-oxazaphosphorine of the cyclohexylamine salt without protector-thio compound of formula II.

The 4-sulfido-oxazaphosphorines of formula I can be used in the combination with the thio compound II in general in a dosage of 0.5 mg to 3500 mg, preferaby 50–2000 mg, especially 200–1400 mg, whereby this amount can be present in dissolved form (for example in aqueous solution or physiological salt solution) or in solid form (for example in a tablet or capsule). This dosage can be dispensed 1 to 10 times daily.

The amount of thio compound of formula II used based on 1 mole of 4-sulfido-oxazaphosphorine of formula I (or its salt) in general is between 0.2–10 moles, especially 0.2–5 moles, preferably 0.4–5 moles. In case the thio compound of formula II contains a $C_2$–$C_6$-sulfoalkyl group, there is used for example 0.2 moles to 3 moles of compound II per 1 mole of 4-sulfido-oxazaphosphorine I. If the thio compound of formula II contains no sulfoalkyl group, as a rule there are used higher doses of thio compound II, for example 1–10 moles of thio compound II to 1 mole of 4-sulfido-oxazaphosphorine I. Thus the mixing ratio of compound I (or its salt) to the thio compound II is 1 mole:0.2 mole up to 1 mole of compound I (or its salt):10 moles of thio compound II, for example 1:1 to 1:10 or 1:1 to 1:5 (in each case in moles). That is, if for example 337 mg of compound I are used (in the case of the 4-(2- hydroxy-ethyl-mercapto)-cyclophosphamide = 1 mmole), then simultaneously or at different times there can be used for example 121 mg to 1210 mg of cysteine (1 mmole to 10 mmole) as thio compound II. In case there is used a different thio compound of formula II there is calculated the corresponding different dosage in mg corresponding to the different molecular weight. In general, the thio compounds of formula II are used in an amount 0.1 mg to 25 grams, preferably 1 mg to 5 grams, especially 10 mg to 5 grams or 10 mg to 3.5 grams, each depending on the amount of 4-sulfido-oxazaphosphorine of formula I used and the special thio compound of formula II used in each case.

For example, the pharmaceutical preparations contain between 30–40 mg of a compound of formula I+2-0–100 mg of cysteine or corresponding molar amounts of another thio compound II and 1230–1300 mg of a compound of formula I+1600–4500 mg of cysteine (or corresponding molar amounts of another thio compound of formula II). Preferred forms of use are solutions which contain between 0.1 and 13% of an active material, whereby this data refers both to a mixture of a 4-sulfido-oxazaphosphorine in formula I and a thio compound of formula II and to corresponding solutions which in each case contain only one component, that is only the 4-sulfido-oxazaphosphorine of formula I and only the thio compound of formula II.

The individual dosage of 4-sulfido-oxazaphosphorine of formula I and thio compound of formula II for example, is with parenteral application between 0.5 mg of compound I+0.3 mg of compound II and 3.5 grams of compound I and 13 grams of thio compound II, preferably between 50 mg of compound I+936 mg of thio compound II and 2 grams of compound I+7 grams of thio compound II, especially between 100 mg of compound I+72 mg of thio compound II and 1.4 grams of compound I+5 grams of thio compound II. With peroral application the individual dosage for example, is at 250 mg of compound I+450 mg of thio compound II. For example, with intravenous injection 1 time daily by injection there can be recommended 1 ampoule having a content of 2–20 ml having 100 mg $P_1$+180 mg of cysteine (or 162 mg of cyclohexylamine salt+146 mg of cysteine) up to 1.0 grams $P_1$+1.8 grams of cysteine (or 1.62 grams of cyclohexylamine salt+1.46 grams of cysteine).

The corresponding is true in regard to the other 4-sulfido-oxazaphosphorines of formula I and the thio compounds of formula II.

The acute toxicity n the NMRI-mouse ($LD_{50}$) of the 4-(2-hydroxy-ethylmercapto-cyclophosphamide) cysteine combination on the mouse for example is with intravenous application 600 mg/kg of 4-(2- hydroxy-2-ethylmercapto)-cyclophosphamide+1100 mg of cysteine.

In general the $LD_{50}$ per kg mouse for the combination 4-sulfido-oxazaphosphorine I+thio compound II is between 300 mg to 1200 mg compound I+108 mg to 2.1 grams thio compound II, preferably between 400 mg to 1000 mg compound I+290 mg to 1.8 grams thio compound II, especially between 500 mg to 800 mg compound I+360 mg to 1.5 grams thio compound II. The maximum tolerated dosage of humans for the combination 4-sulfido-oxazaphosphorine I with thio compound II in the range of the molar mixture ratios 1:2–1:5 is about at 50 mg/kg (body weight/human), based on the 4-sulfido-oxazaphosphorine component.

The combination can be used in human medicine and in veterinary medicine alone or with other pharmacologically active materials.

The cytostatic effect of the combination of the invention depends on the effect of the 4-sulfido-oxazaphosphorine of formula I. However, these are in general not very well suited for true healings in general because of their high local toxicity. Only those 4-sulfido-oxazaphosphorines of formula I where $R_5$ forms a $C_2$–$C_6$-sulfidoalkyl group are considerably less toxic and can even be used alone, that is without using the combination with thio compounds of formula II.

The effect of 4-sulfido-oxazaphosphorines of formula I (except those where $R_5$ forms a $C_2$–$C_6$-sulfidoalkyl group) proceeds from the following:

For example, the $CD_{50}$ ($CD_{50}$ = curative dosage; this is the dosage at which 50% of the tumor carrying animals are healed. The $CD_{50}$ was determined according to: Ther, Grundlagen der experimentellen Arzneimittelforschung, Verlagsgesellschaft Stuttgart, (1965). With intraperitoneal injection with the NMRI mouse on the 3rd day after transplantation of $10^6$ S180 tumor cells/mouse the $CD_{50}$ was 18 mg/kg body weight mouse. With a single dosage of 110 mg/kg 95% of the animals were healed. For example, the lowest cancerotoxic effective dosage at intraperitoneal application is 2.5 mg/kg. As a general dosage range for the effect in the previously mentioned animal experiments for example, in intraperitoneal application there can be used a range between 5 mg/kg to 100 mg/kg, preferably 20 to 100 mg/kg.

In the use of the 4-sulfido-oxazaphosphorine of formula I alone, that is without a combination with a thio compound of formula II, the corresponding pharmaceutical preparation can contain for example 0.25–1500 mg, preferaby 50–1250 mg, especially 300–1000 mg, of 4-sulfido-oxazaphorphorine. Here likewise preferred forms of use are solutions (aqueous or in physiological salt solution) which contain between 0.5 and 3% of the active 4-sulfido-oxazaphosphorine. The individual dosage of 4-sulfido-oxazaphosphorine for example, can be: in intravenous dosage between 20 and 1250 mg; by intraperitoneal and intrapleural injection between 0.25 and 1500 mg, preferably between 50 and 1250 mg. For example, there can be recommended with intravenous injection 1 ampoule having a content of 1–5 ml and 50 to 200 mg of 4-sulfido-oxazaphosphorine of formula I. The use of 4-sulfido-oxazaphosphorines of formula I alone can be carried out by organ perfusion or by the chemotherapy of pleurametastases.

The $LD_{50}$ on the NMRI mouse for the 4- sulfido-oxazaphosphorine of formula I where $R_5$ is the $C_2$–$C_6$-hydroxyalkyl group, the glutathionyl group or the —$CH_2$—$CH(NH_2)$-COOH group which is optionally acylated on the N-atom in sole use is in intravenous application 250–470 mg/kg and in intraperitoneal appliication 200-300 mg/kg body/mouse. The $LD_{50}$ of such 4-sulfido-oxazaphosphorines of formula I wherein $R_5$ is the $C_2$-$C_6$-sulfoalkyl group is for example in intravenous application (rat) 316 mg/kg, in intraperitoneal application (mouse) 300 mg/kg; in oral application (mouse) above 1000 mg/kg.

Those 4-sulfido-oxazaphosphorines of formula I where $R_5$ is a $C_2$-$C_6$-sulfoalkyl group or a salt thereof generally are more strongly effective and less toxic than the other compounds within formula I. The $LD_{50}$ for this group of compounds in single intravenous application is for example, around 300-470 mg/kg; accordingly they have an around 20-50% less acute toxicity than the standard preparative cyclophosphamide ($LD_{50}$ in single intravenous dose 244 mg/kg) while it shows the same curative activity as the cyclophosphamide. Thus for example, the average curative dosage in the case of lymphatic leukemia L5222 of the rat (strain BD IX) in a single intravenous application on the 5th day after inoculation of the leukemia with 4-sulfido-oxazaphosphorines of formula I where $R_5$ forms a $C_2$-$C_6$-sulfidoalkyl or its salts, likewise for cyclophosphamide the dosage is 1.5 mg/kg and in the chemosensitive Yoshida-ascitescarcinosa (Line AH13) of the Aprague-Dawley rats, 1 mg/kg.

The reduction of the toxicity by the compounds of formula I through the combination of the invention with thio compounds of formula II for example, is clear from the following experiments:

Acute Toxicity

Determination according to: Ther, Grundlagen der experimentellen Arzneimittelforschung, Verlagsgesellschaft MBH, Stuttgart, (1965).

The acute toxicity of 4-(2- hydroxyethylmercapto)-cyclophosphamide ($P_1$) for example, for intravenous and intraperitoneal application with female NMRI-mice (20-25 g) is determined as follows:

|  | in mg/kg $LD_{50}$ (30 days observation time) | in mg/kg $LD_{50}$ (90 days observation time) |
|---|---|---|
| $P_1$ intraperitoneally | 238 | 160 |
| $P_1$ intravenously | 290 | 215 |
| $P_1$ + 5 fold molar amount of L (+)-cysteine intraperitoneally | 715 | 715 |
| $P_1$ + 5 fold molar amount of L (+)-cysteine intravenously | 600 |  |

The cysteine thereby was dissolved in physiological NaCl (isotonic salt solution) and injected. Injection volumes always 20 ml/kg (cysteine solutions must be prepared fresh especially for intravenous and intraperitoneal injections).

$P_1$ likewise is always dissolved fresh in physiological NaCl (0.5-2.5% solution) and injected directly after the cysteine injection.

The given $LD_{50}$ values for the intraperitoneal injection of $P_1$ and $P_1$+cysteine (1 mole $P_1$:5 moles cysteine) refers to injection volumes in each case of 20 ml/kg of body weight. In increasing the injection volume to 10 fold the amount (200 ml/kg there is increased for example, the $LD_{50}$ for $P_1$ to 460 mg/kg and that of $P_1$+cysteine (mole ratio 1:5) to 1090 mg/kg (based on the $P_1$ component). In increasing the injection volume in intraperitoneal injection around a factor of 10 there was caused accordingly a reduction of the total toxicity to 54-68% of the toxicity which was determined in the smaller injection volume.

As stated above, the thio compound II in intraperitoneal injection of $P_1$ causes an increase of the $LD_{50}$ around a factor of 4.5 (with 90 days observation time). In intravenous injection the reduction in toxicity is dependent on the duration of injection. Thus at an injection duration of 1 minute the $LD_{50}$ of $P_1$+5 fold molar amount of cysteine is 600 mg/kg and drops in quicker injection (bolus injection) to 330 mg/kg, while the $LD_{50}$ of $P_1$ itself is 290 mg/kg. The detoxifying action of cysteine in intravenous injection thus is caused only in longer (slower) duration of injection (longer than 1 minute).

After the intraperitoneal injection of $P_1$ and cysteine in the mice there were observed neither injury or pathological changes of the abdominal cavity nor modification and glycogen loss of the liver cells or blood vessel disturbances (for example in subperitoneal arteries).

The reduction of the toxicity of compounds of formula I is reduced with increasing portions of the thio compounds of formula II. The relative protective effect is the strongest in the lower range of the mixing ratio, for example in the range of 1 mole parts by weight compound I to up to 2 moles parts by weight thio compound of formula II. In the connected range (1 mole parts by weight compound I to 2-10 moles parts by weight thio compound II) the toxicity reduction drops relatively more slowly.

Subchronic Toxicity 4-(2-hydroxy-ethylmercapto)-cyclophosphamide ($P_1$)+cysteine (molar ratio 1:5) NMRI-mouse.

In intraperitoneal injection in each case of 383 mg/kg $P_1$+685 mg/kg cysteine (20 ml aqueous solution/kg) corresponding to 53% of the $LD_{50}$ for this combination in the weekly interval, there dies after 6 injections 2 of 8 animals. Thereby in all there were injected 6.8 mmol/kg of $P_1$+34 mmol/kg of cysteine. Cyclophosphamide according to the same pattern (without cysteine) for example already with 3 mmol/kg total dosage resulted in the deaths of 6 mice.

$P_1$+cysteine (molar ratio 1:5; dog: 30 mg/kg $P_1$+54 mg cysteine (1:5 moles) weekly intravenous injection 11 ml of aqueous solution/kg dog). There was observed no damage to the activity and only slight weight loss. Deaths of the animals after 4 weeks with the total dosage of 120 mg/kg $P_1$+216 mg cysteine Section: No macroscopic found, especially no hint for a cystitis. In the blood a lesser drop of leucocytes and thrombocytes.

Local Toxicity

Rabbits—bladder ($P_1$ cysteine 1:5 mol):

Single instillation (introduction of fluid in an organ over a certain time span by means of a catheter) of 1.35 grams $P_1$+2.43 grams of cysteine in 25 ml of distilled water (solubility limit) in the bladder of female rabbits—hybrids (about 4 kg weight) for 30 minutes: residence time: 30 minutes, histological finding 3 days after instillation: inconspicuous bladder mucous membrane without recognizable indication of cystitis: Animal alive 10 months after the instillation.

Three instillations in each case 1 day apart into the bladder of female rabbits having implanted Brown-Pearce sarcomas: other conditions as above. Local toxicity macroscopically: slight thickening of the bladder wall, no bleeding, no or only a trifle necrotization. Histological: Urothel in wide extent intact, in spots trifling edematous and inflammatory damage outside the tumor implant detectable in the region of the normal urethra.

Three times instillation in daily succession, other conditions as above. Macroscopic finding: thickened bladder wall with bleeding and slight mecrotic region, histological: only slight urothel present, bladder wall changed edematosly inflammed. Dog bladder: female beagles (dog) about 15 kg weight, were in each case injected with 50 ml of a solution of 2.7 grams $P_1 + 4.84$ grams of cysteine in 50 ml of distilled water at room temperature. Residence time: 30 minutes. Cytoscopic finding: in each case 1 week after installation: bladder mucous membrane inconspicous, no indication for cystitis. Repetition of the instillation after 3 months. Cytoscopic after 1 week after the instillation: Inconspicous bladder mucous membrane, no indication for cystitis.

The pharmacological action of the combination of the invention and the 4-sulfido-oxazaphosphorine of formula I for example, is clear from the following experiments:

Local (intracavitary) Chemotherapy (a) In leukemia (L1210-leukemia cells) on the mouse:
0.5 hours after inoculation of $5 \times 10^5$ L1210-leukemia cells per mouse (DBA$_2$/Hans+) (specific mouse strain of female mice which are used for experimental purposes in tumor investigations and for example, can be obtained from the Zentralinstitut fur Versuchstierforschung in Hannover, Germany) were given therapy by a single intraperitoneal injection of $P_1$ (curative dosage 68 mg/kg) or $P_1$+cysteine (mole ratio 1:5). The curative dosage for $P_1$ in the combination with the cysteine was 90 mg/kg. The therapeutic breadth TI$_{50}$ (quotient of LD$_{50}$ and CD$_{50}$) for $P_1$ alone is: 3.5 and for $P_1$+cysteine on the contrary is 7.3. There were used in each case physiological salt solutions (20 ml solution/kg mouse). The time of injection was always less than 1 minute.

(b) In S180 sarcoma in the ascites from (NMRI-mouse):
Therapy through single intraperitoneal injection (time of injection less than 1 minute) of $P_1$ of $P_1$+cysteine in physiological salt solution (mole ratio 1:5, 10 ml solution per kg mouse) 3 days after transplantation of $10^6$ tumor cells per mouse. For $P_1$ alone the CD$_{50}$ is 18 mg/kg; for $P_1$+cysteine (mole ratio 1:5) 32 mg/kg; the corresponding TI50 values for $P_1$ are 13 for 30 days and 9.7 for 60 days observation; for the combination $P_1$+cysteine (mole ratio 1:5) on the contrary there was a value of 23 for 60 days observation. In both tumors there was thus approximately a doubling of the therapeutic breadth through the addition of cysteine.

(c) Brown-Pearce-sarcoma in the bladder of rabbits:
Rabbit hybrids were implanted with about $10^7$ cells of a Brown-Pearce-sarcoma under the submucosa (cell layer below the mucous membrane). Four days after tumor implantation the intracavitary chemotherapy begins through instillation of 160 millimoles $P_1$+800 millimoles cysteine (mole ratio 1:5) in 25 ml of distilled water having a temperature of 37° C. for 30–60 minutes. Altogether there were 3 repetitions with a 1 day interval in each case.

Histological section of the bladder wall show a clear response of the tumor to the therapy with large surface necrotic regions. Characteristic is the necrolization of the periphery of the tumor implant here in contrast to spontaneous, centrally situated necroses in the untreated controls. The size of the tumors is 5–25 mm in diameter. At the end of the experiment the endothelium is free of tumor without histological changes.

Systemic chemotherapy (the active material is brought into the body via the blood vessels) with Human Tumor Cells (tumor xenografts, carrying human tumor cells to experimental animals).

On thymusaplastic nu/nu mice (nu/nu mice=plain mice which have the genetic deficiency of missing immune defenses)

(The experimental procedure was carried out as follows according to: C. O. Polvsen, G. K. Jacobsen, J. Rygaard, The Laboratory Animal in Drug Testing, Editor A. Spiegel, pages 63–73, Fischer-Verlag, Stuttgart, (1973).

(a) Human mammary-carcinoma from operation material of a women's clinic were heterotransplanted to thymusaplastic nu/ny mice. After the 23–25th passage in each case by implantation of a thin tumor section having a diameter of 8–10 mm into the milk ducts after growth of the implants to 0.15–0.25 grams the animals were subjected to therapy and the curative effect determined through measuring the tumor surface.

After a single intraperitoneal injection (time of injection less than 1 minute) of 10 ml of an aqueous solution of 98 mg $P_1$+176 mg cysteine/kg mouse there was clear retardation of the tumor growth in comparison to the untreated controls. With a single intraperitoneal injection (time less than 1 minute) of 296 mg/kg $P_1$+535 mg cysteine (corresponding to about 40% of LD$_{50}$) in aqueous solution (10 ml/kg mouse) there occurred a checking of the tumor growth which corresponds with the one that can be produced with a single injection of 100 mg/kg of cyclophosphamide in physiological salt solution (10 mg/kg mouse) as standard comparison material, while the untreated controls during the same period of observation (3 weeks) had a 4 fold tumor surface increase with the corresponding proportional increase in weight.

With multiple injections intraperitoneally in each case of 250 mg/kg $P_1$+450 mg/kg of cysteine (aqueous solution in each case 10 ml mg/kg mouse) in each case in weekly intervals (time of injection less than 1 minute), in a time span of 5 weeks there was reached a reduction of the tumor mass in the thought of a true curative healing, which corresponds to the effect of 150 mg/kg cyclophosphamide, likewise injected in weekly intervals. The untreated controls died within the time span of observation of 5 weeks.

The (subchronic) toxic effects of $P_1$ in combination with cysteines, however, are in this use clearly less than those of cyclophosphamide, which is recognizable through the considerably improved general condition.

(b) Human cornified bladder carcinoma on the nu/nu mouse:
A chemotherapy resistance female cornified bladder carcinoma from the operation material of a urological clinic was transplanted after the 4th passage to male nu/nu mice. Systemic chemotherapy was obtained by 5 intraperitoneal injections of 250 mg/kg $P_1$ (=0.74 mmole/kg mouse)+449 mg/kg cysteine (aqueous solution; 10 ml/kg mouse) in each case at weekly intervals or 5 times intraperitoneal injection of cyclophosphamide (150 mg/kg=0.53 mmole/kg) in the same interval. In comparison to the controls which were dead 18 days after beginning the experiment, $P_1$+5 fold the molar amount of cysteine with repeated use stops the growth of the tumor and results in survival of the animals. The cancerostatic effect corresponds to that of cyclophosphamide as the standard material in a dosage of 150 mg/kg corresponding to ⅔ molar equivalents.

The isolated extremity perfusion is a process for the cytostatic treatment of malign tumors of the extremities, whereby the rest of the organism is not exposed to the effect of cytostatica.

As the animal model for this process there is employed the isolated perfusion of the tumor carrying (Yoshida sarcoma) rat legs, whereby the tumor growth is meaasured after empty perfusion and cytostatica perfusion.

After 10 minutes perfusion with $P_1$ (500 nmole/ml) +cysteine ( 5 fold, molar), there was produced a complete healing of the animals, likewise with perfusion with a solution of 10,000 nmoles/ml. The animals were still free of recidification one-half year after the experiment.

Perfusion with $P_1$ alone was less successful. With 5000 nmoles/ml two animals died after the perfusion with 2000 nmoles/ml besides a retardation of the growth of the tumor there was observed merely a healing with two of the 4 animals.

The production of the pharmaceutical preparations which contain the 4-sulfido-oxazaphosphorine of formula I and/or thio compound of formula II occurs according to methods that are generally known, as is explained subsequently in illustrative examples for different injection solutions.

The compositions can comprise, consist essentially of, or consist of the stated materials.

Detailed Description

EXAMPLE 1

Combination preparation containing as active material in each case 50 mg (=0.15 millimoles) of 4-(2-hydroxy-ethyl-mercapto)-cyclophosphamide ($P_1$) and L-cysteine in different molar ratios (2X, 5X, and 10X) based on the material $P_1$ according to the following summary:
One Injection Flask Contains:

|  | Preparation 1 | Preparation 2 | Preparation 3 |
| --- | --- | --- | --- |
| Materials $P_1$ | 50.0 mg (0.15 millimole) | 50.0 mg | 50.0 mg |
| L-Cysteine | 36.0 mg (0.3 millimole) | 90.0 mg (0.75 millimole) | 180.0 mg (1.5 millimole) |
| D-Mannitol | 200.0 mg | 110.0 mg | — |
| Water for injection purposes up to | 2.0 ml | 2.0 ml | 2.0 ml |

As alkali oxides there are used for example $Na_2O$ and $K_2O$ and as alkaline earth metal oxides MgO, CaO, SrO, and BaO. The materials $P_1$, L-cysteine and, in case it is necessary, D-mannitol, in each case while gassed with nitrogen are dissolved in sufficient water that there is formed a solution having a volume of 2 ml and subjecting the solution to a sterile filtration in known manner. This solution was then doesed into brown 10 ml injection flasks under aseptic conditions, provided with freeze drying stoppers and lyophilized in a freeze drying plant. Subsequently the freeze drying plant was gassed with dry nitrogen and the ampoule flasks closed in the plant.

The contents of the ampoule flasks were dissolved in 5 ml of water for injection purposes for the production of applicable injection solution.

Preparation for the separate use of 4-sulfido-oxazaphosphorines I and thio compounds II.

EXAMPLE 2

As stated in Example 1 50.0 mg (0.15 millimole) of 4-(2-hydroxy-ethylmercapto)-cyclophosphamide ($P_1$) and 250.0 mg of D-mannitol were dissolved with water (for injection purposes) to a solution having a volume of 2 ml and lyophilized.

EXAMPLE 3

As stated in Example 1 36.0 mg (0.3 millimole) of cysteine and 220.0 mg of D-mannitol were dissolved with water (for injection purposes) to form a solution having a volume of 2 ml and lyophilized. In the same manner there were produced lyophilisates of cysteine which contained:

90 mg (0.75 millimole) of L-cysteine and 140.0 mg of D-mannitol as well as 180 mg (1.5 millimole) of L-cysteine (without the addition of mannitol).

The contents of the ampoule flasks according to Examples 2 and 3 were dissolved in each case in 5 ml of water (for injection purposes) for the production of injection solutions.

EXAMPLE 4

Combination preparations containing as active materials in each case 82 mg (=0.15 millimole) "Cyclohexylamine salt" and L-cysteine in different molar ratios (2X, 5X, and 10X) based on the material "Cyclohexylamine salt" according to the following summary:

Cyclohexylamine salt=3[2-(bis-(2-chloroethyl)-amino-2-oxo-tetrahydro-2H-1,3,2-oxazaphosphorine-4-yl-thio]-2-mercaptopropanesulfonic acid cyclohexylamine salt:
One Injection Flask Contains:

|  | Preparation 1 | Preparation 2 | Preparation 3 |
| --- | --- | --- | --- |
| Materials Cyclohexylamine salt | 82 mg (0.15 millimole) | 82 mg | 82 mg |
| L-Cysteine | 36.0 mg (0.3 millimole) | 90.0 mg (0.75 millimole) | 180.0 mg (1.5 millimole) |
| D-Mannitol | 200.0 mg | 110.0 mg | — |
| Water for injection purposes up to | 2.0 ml | 2.0 ml | 2.0 ml |

The materials "Cyclohexylamine salt", L-cysteine and, if necessary, D-mannitol in each case with gassing with nitrogen were dissolved in a sufficient water that there was formed a solution having a volume of 2 ml and subjected to a sterile filtration in known manner. This solution was then dosed under aseptic conditions into brown 10 ml injection flasks, provided with freeze drying stoppers and lyophilized in a freeze drying plant. Subsequently the freeze drying plant was gassed with dry nitrogen and the ampoule flasks closed in the plant.

The contents of the ampoule flasks were dissolved in 5 ml of water (for injection purposes) for the production of the applicable injection solution.

Preparations for the separate use of 4-sulfido-oxazaphosphorines I and thio compounds II.

EXAMPLE 5

As stated in Example 4 82 mg (0.15 millimole) of "Cyclohexylamine salt" and 250.0 mg of D-mannitol were dissolved with water (for inejection purpose) to a solution having a volume of 2 ml and lyophilized.

EXAMPLE 6

As stated in Example 4 36.0 mg (0.3 millimole) of cysteine and 220.0 mg of D-mannitol were dissolved with water (for injection purpose) to form a solution having a volume of 2 ml and lyophilized. In the same manner there were produced lyophilisates of cysteine which contain:

90 mg (0.75 millimole) of L-cysteine and
140.0 mg D-mannitol as well as
180 mg (1.5 millimoles) of L-cysteine without addition of mannitol).

The contents of the ampoule flasks in accordance with Examples 2 and 3 were dissolved in each case in 5 ml of water (for injection purposes) for the production of injection solutions.

Example of Production

EXAMPLE A 2-(2-chloro-ethylamino)-3-(2-chloro-ethyl)-4-(2-hydroxy-ethylthio)-tetrahydro-2H-1,3,2-oxazaphosphorine-2-oxide $$Cl-CH_2-H_2-HN\underset{O}{\overset{O}{\diagdown}}\underset{P2}{\diagup}\underset{1}{\overset{N\diagup 3}{\diagdown}}\underset{CH_2}{\overset{CH_2-Cl}{\overset{|}{|}}}S-CH_2-CH_2-OH$$

5.4 grams (19 mmoles) of 4-hydroxy ifosfamide 4-hydroxy-2-(2-chloro-ethylamino)-3-(2-chloro-ethyl)-tetrahydro-2H-1,3,2-oxazaphosphorine-2-oxide were suspended in 40 ml of methylene chloride, treated with 2.8 ml (30 mmole) of 2-mercaptoethanol, cooled to 5° C., 150 mg of trichloroacetic acid added with stirring, after 3 days concentrated at 4° C., the oil purified on silica gel, eluting with chloroform/methanol (15:1 by volume) and acetone/methylene chloride (3:1 by volume).

Yield: 3.4 grams (53% of theory)
$R_f$ value 0.45
Elutent: Chloroform/methanol (5:1 by volume)
Coloration: Iodine

EXAMPLE B 2-(Bis-2-chloro-ethylamino)-4-[3-hydroxy-2-mercapto-propyl-(1)-thio]-tetrahydro-2H-1,3,2-oxazaphosphorine-2-oxide $$(Cl-CH_2-CH_2)_2N\underset{O}{\overset{O}{\diagdown}}\underset{P}{\diagup}\underset{O}{\overset{NH}{\diagdown}}SH-CH_2-\underset{|}{\overset{SH}{\overset{|}{CH}}}-CH_2-OH$$

4-hydroxy-cyclophosphamide is reacted with 5 fold the amount of 2,3-mercapto-1-propanol in acetone at 4° C. After 2 hours the acetone was drawn off in a water jet vacuum under cooling. The residue was separated on a silica gel plate by preparative thin layer chromatography using ethyl acetate/acetone (1:1 by volume as the mobile phase. $R_f=0.4$; Proof of the alkylating activity ($\gamma$-nitrobenzyl pyridine) and iodine-acid on thio groups. The zone at $R_f$ 0.4 was extracted in the cold with methylene chloride and the microcrystalline crude produce obtained by precipitation with diethyl ether. Melting point (uncorrected): 90°–95° C.

The products of the invention can be used to combat cancer or for immunosuppression in animals, e.g. mammals such as humans and other animals, e.g. rats, dogs, cats, and mice.

The entire disclosure of German priority application Nos. P 3151977.6 and P 32220006.5 are hereby incorporated by reference.

Example for the prevention of venus pain

During clinical phase I trials with mafosfamide (3/2-(bis-(2-chloroethyl)-amine-2-oxo-tetrahydro-2H-1,3,2-oxazaphosphorine-4-yl-thio-ethanesulfonic acid), cyclohexylamine salt and mafosfamide lysine salt it was found that pain along the injected vein constituted a severe side effect at a dose of 400 mg/m² and made dose escalations beyond 1000 mg/m² impossible.

However, these doses were still below the expected myelosuppresive doses. Dilution of the compound or prolongation of the infusion time had only marginal effects on the severe and dose-limiting side effect. None of the patients showed signs of phlebitis or tissue inflammation at the injection site. The quality of the pain was frequently described as "cramplike" neuralgia and apparently persisted in some patients for several weeks. No suggestions or hints were encountered during the preclinical investigations with mafosfamide that such a phenomenon might occur. Therefore, in order to further elucidate the nature and specificity of the pain and to possibly design preventive measures, a simple and predictive animal model had to be developed. This model as well as results of studies investigating the mechanism of mafosfamide-induced venous pain are set forth below.

Material and Methods

Animals: Outbread Sprague-Dawles rats (180–230 g) were obtained from Mus Rattus GmbH (Brunnthal, F.R.G.). The animals were housed under standard conditions, fed pellet diet (Altromin ® 1324) and had tap water ad libitum. A 18 gauge needle was placed into the lateral tail vein and was connected to an infusion pump. Thereafter, the animal was put into a semirestraining tube made of a stainless steel net. This tube allowed normal sensory contact with the environment and fixed the animal without pressure. Normal saline was infused at room temperature at a speed of 1 ml/hour. Generally, within 30 minutes of infusion the animals felt comfortable and were asleep. At this stage the test agent was injected by switching to a parallel infusion. In case of irritation, the animals became awake and made escape and defense movements, the experiment was subsequently terminated.

Test substances: All chemicals were either synthesized in the Department of Chemistry, Asta-Werke AG (Vielefeld, F.R.G.), or purchased from commercial sources. Dilution of test reagents were done with normal saline. In groups of five animals the approximate threshold concentration of each drug which reproducibly induced a reaction was determined.

Results

Table 1 summarizes the test compound and their respective, approximate threshold pain-inducing concentration. Neither saline, Ringer's solution, hydrochloric acid (pH 4) nor cyclophosphamide (below 30 mg/ml) or ifosfamide (below 10 mg/ml) induced any reaction. In contrast, mafosfamide cyclohexylamine salt (ASTA Z 7557) and mafosfamide lysine salt (ASTA Z 7654) caused pain at concentrations of 1 mg/ml. In a similar experiment various concentrations of sodium 2-mercaptoethane sulfonate (mesna) or N-acetyl-cysteine (NAC) were added. As can be seen, a 5 molar mesna or NAC solution completely prevented the pain-inducing effect of mafosfamide lysine salt.

TABLE 1

Approximate threshold concentration of various compounds inducing venous pain in the sleeping rat model (+ = reaction, − = no reaction)

| Compound | Reaction | Concentration (mg/ml) |
| --- | --- | --- |
| Normal Saline | − | − |
| Ringer's Solution | − | − |
| HCl pH 4 | − | − |
| Cyclophosphamide | + | 30 |
| Ifosfamide | + | >10 |
| ASTA Z 7557 | + | 1 |
| ASTAA Z 7654 | + | 1 |
| ASTA Z 7654 + 5 m Mesna | + | >5 |
| ASTA Z 7654 + 5 m NAC | + | >5 |

What is claimed is:

1. A process for reducing the pain associated with administering, by injection into the vein of a human or other animal host, a first amount, effective to combat cancer or immune suppression, of a 4-sulfido-oxazaphosphorine of the formula

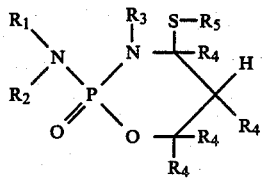

where $R_1$, $R_2$, and $R_3$ are hydrogen, methyl, ethyl 2-chloroethyl, or 2-methanesulfonyloxyethyl and at least two of them are taken from the group consisting of 2-chloroethyl and 2-methanesulfonyloxyethyl, $R_4$ is hydrogen or methyl $R_5$ is a $C_2$–$C_6$-hydroxyalkyl group or a $C_2$–$C_6$-mercaptoalkyl group or each of these groups with an additional mercapto group, or $R_5$ is a carboxy-$C_1$–$C_{10}$-alkyl, a carb-$C_1$–$C_6$-alkoxy-$C_1$–$C_{10}$-alkyl group, a 2-amino-2-carboxyethyl group, a 2-amino-2-carb-$C_1$–$C_6$-alkoxy-ethyl group, a 2-$C_2$–$C_6$-alkanoylamino-2-carboxyethyl group, a 2-$C_2$–$C_6$-alkanoylamino-2-carbo-$C_1$–$C_6$-alkoxy-ethyl group, the glutathionyl group, a $C_2$–$C_6$-sulfoalkyl group, or a $C_2$–$C_6$-sulfoalkyl group which contains a mercapto group or a physiologically compatible salt thereof comprising simultaneously administering to the vein a second amount of a thio compound of the formula:

where $R_6$ is the glutathionyl group or a $C_2$–$C_6$-alkyl group which is substituted once or twice by a hydroxy group, mercapto group, amino group, a $C_2$–$C_6$-alkanoyl-amino group, sulfo group, a carbo-$C_1$–$C_6$-alkoxy group, or carboxy group and $R_7$ is hydrogen or $R_7$ is a $C_2$–$C_6$-sulfoalkylthio group if $R_6$ represents a $C_2$–$C_6$-sulfoalkylthio group or a physiologically compatible salt of the compound of formula II and the second amount of said compound of formula II being effective to reduce the pain associated with injecting the first amount of the compound of formula I into the vein.

2. A process according to claim 1 wherein $R_5$ is a $C_2$–$C_6$-hydroxyalkyl group, a $C_2$–$C_6$-mercaptoalkyl group or each of these groups with an additional mercapto group, a 2-amino-2-carboxyethyl group, a 2-$C_2$–$C_6$-alkanoylamino-2-carboxyethyl group, a 2-$C_2$–$C_6$-alkanoylamino-2-carb-$C_1$–$C_6$-alkoxy-ethyl group, the glutathionyl group, a $C_2$–$C_6$-sulfoalkyl group or a $C_2$–$C_6$-sulfoalkyl group which contains a mercapto-group or a physiologically compatible salt thereof.

3. A process according to claim 1 wherein $R_5$ is a hydroxyethyl group, a mercaptoethyl group, a carboxyethyl group, a 2-amino-2-carboxyethyl group, an acetylamino-2-carboxyethyl group, a acetylamino-2-carb-ethoxy-ethyl group, the glutathionyl group, a sulfoethyl group, or a physiologically compatible salt thereof.

4. A process according to claim 3 wherein the thio compound is cysteine, cysteine-methyl- or ethyl-ester, N-acetyl-cysteine, cysteine hydrochloride, cysteine ascorbate, N-acetyl homocysteine, penicillamine, 2,3-dimercapto-1-propanol or pharmacologically acceptable salt of a mercapto alkane sulfonic acid having the formula HS-alk-SO$_3$H wherein alk is a member selected from the group consisting of a straight or branched $C_2$–$C_6$-alkylene group.

5. A process according to claim 1 wherein the thio compound is cysteine, cysteine-methyl- or ethyl-ester, N-acetyl-cysteine, cysteine hydrochloride, cysteine ascorbate, N-acetyl homocysteine, penicillamine, 2,3-dimercapto-1-propanol or the sodium salt of 2-mercapto-ethane sulfonic acid.

6. A process according to claim 1 wherein the 4-sulfido-oxazaphosphorine is 4-(2-sulfoethylmercapto)-cyclophosphamide, 4-(2-sulfoethylmercapto)-ifosfamid, or 3-[2-[bis-(2-chloroethyl)-amine-2-oxo-tetrahydro-2H-1,2,2-oxazaphosphorine-4-yl-thio]-2-mercapto propanesulfonic acid, all in form of their cyclohexylamine or lysine salts and the thio compound is N-acetyl-cysteine or the sodium salt of 2-mercaptoethane-sulfonic acid.

7. A process according to claim 6 wherein the N-acetyl-cysteine is L-N-acetyl-cysteine.

8. A process according to claim 1 there is administered 0.5 to 3500 mg of 4-sulfido-oxazaphosphorine and 1 to 10 moles of thio compound per mole of 4-sulfido-oxazaphosphorine.

9. A process according to claim 1 wherein there is employed 0.1 mg to 25 grams of the thio compound and the amount of thio compound of formula II is 1–10 moles from the mole of the mole of the compound of formula I.

10. A process according to claim 7 wherein the 4-sulfide-oxazaphosphorine is 4-(2-sulfoethylmercapto)-cyclophosphamide.

11. A process according to claim 1 wherein the thio compound is N-acetyl-cysteine or 2-mercapto-ethane sulfonic acid (sodium salt) and the 4-sulfide-oxazaphosphorine is 4-(2-sulfoethylmercapto)-cyclophosphamide.

12. A process according to claim 5 wherein the thio compound is other than 2,3-dimercapto-1-propanol.

13. A process according to claim 1 wherein $R_6$ is a $C_2$–$C_6$-alkanoyl amino group.

14. A process according to claim 1 wherein in formula I $R_1$ and $R_2$ are hydrogen or 2-chloroethyl and $R_3$ is hydrogen or 2-chloroethyl and at least two of $R_1$, $R_2$, and $R_3$ are 2-chloroethyl, $R_4$ is hydrogen and $R_5$ is 2-hydroxyethyl, 2-sulfoethyl, 2-amino-2-carboxyethyl or glutathionyl.

15. A process according to claim 4 wherein in formula I $R_1$ and $R_2$ are hydrogen or 2-chloroethyl and $R_3$ is hydrogen or 2-chloroethyl and at least two of $R_1$, $R_2$, and $R_3$ are 2-chloroethyl, $R_4$ is hydrogen and $R_5$ is 2-hydroxyethyl, 2-sulfoethyl, 2-amino-2-carboxyethyl or glutathionyl.

16. A process according to claim 15 wherein $R_1$ and $R_2$ are 2-chloroethyl and $R_3$ is hydrogen.

17. A process according to claim 14 wherein $R_1$ and $R_2$ are 2-chloroethyl and $R_3$ is hydrogen.

18. A process according to claim 1 wherein $R_6$ is $C_2$–$C_6$-alkyl substituted in $\omega$-position by a sulfo group, glutathionyl, 2-hydroxyethyl, 2-mercaptoethyl, 2-aminoethyl, or 2-carboxyethyl, 2-carboxy-2-acetylamino-ethyl and $R_7$ is hydrogen.

19. A process according to claim 14 wherein $R_6$ is 2-sulfo-ethyl, glutathionyl, 2-hydroxyethyl, 2-mercaptoethyl, 2-aminoethyl, or 2-carboxyethyl, 2-carboxy-2-acetylamino-ethyl and $R_7$ is hydrogen.

20. A process according to claim 1 wherein the compound of formula I and the compound of formula II are administered to a host which is a human, dog, cattle, horse, sheep, cat or rat.

21. A process according to claim 20 wherein the host is a human.

22. A process according to claim 8 wherein the compound of formula I and the compound of formula II are administered to a host which is a human, dog, cattle, horse, sheep, cat or rat.

23. A process according to claim 22 wherein the host is a human.

* * * * *